(12) United States Patent
Adair

(10) Patent No.: US 7,067,276 B2
(45) Date of Patent: *Jun. 27, 2006

(54) METHOD OF USING METALOPORPHYRINS FOR TREATMENT OF ARTERIOSCLEROTIC LESIONS

(76) Inventor: Edwin L. Adair, 317 Paragon Way, Castle Pines Village, CO (US) 80104

(*) Notice: Subject to any disclaimer, the term of this patent is extended or adjusted under 35 U.S.C. 154(b) by 258 days.

This patent is subject to a terminal disclaimer.

(21) Appl. No.: 10/836,453

(22) Filed: Apr. 30, 2004

(65) Prior Publication Data

US 2004/0202609 A1 Oct. 14, 2004

Related U.S. Application Data

(63) Continuation-in-part of application No. 10/215,881, filed on Aug. 8, 2002, now Pat. No. 6,753,160, which is a continuation-in-part of application No. 10/176,558, filed on Jun. 21, 2002, now Pat. No. 6,750,037.

(51) Int. Cl.
C12Q 1/02 (2006.01)
A61K 49/00 (2006.01)
A61K 49/04 (2006.01)

(52) U.S. Cl. .................. 435/29; 424/9.1; 424/9.4; 424/9.362; 424/569

(58) Field of Classification Search ............ 435/29; 424/9.1, 9.4, 9.362, 569
See application file for complete search history.

(56) References Cited

U.S. PATENT DOCUMENTS

| 3,394,369 A | 7/1968 | Rebeiz ................... 47/58 |
| 3,846,490 A | 11/1974 | Aronova et al. ......... 562/567 |
| 3,973,129 A | 8/1976 | Blumberg et al. ...... 250/461 B |

(Continued)

FOREIGN PATENT DOCUMENTS

| EP | 0 277 837 | 8/1988 |
| JP | 04330013 A | 11/1992 |
| JP | 408295639 A | 11/1995 |
| WO | WO 02/096366 | 12/2002 |

OTHER PUBLICATIONS

Palac et al, Nuclear Medicine Communications, V.10 (11), pp841–50, (Nov. 1989) Abstract Only.*
Arternov et al., Cancer Res., 61:3039–3044 (2001).
Fiel et al., Cancer Letters, 40:23–32 (1988).

(Continued)

Primary Examiner—Louise N. Leary
(74) Attorney, Agent, or Firm—Sheridan Ross PC

(57) ABSTRACT

A method for treating arteriosclerotic lesions is provided wherein the method is characterized by administering a chemical compound to the patient, the compound being a porphyrin complexed with a radioactive metal. Cells which exhibit an affinity for the porphyrin element indicate sites of plaque buildup. The radioactive metal within the compound is cytotoxic to cells in and surrounding the plaque and may allow tomographic scanning of the plaque as well. The complexed compound can be introduced to the patient a desired number of times to provide the necessary radiation treatment and ongoing monitoring of plaque removal.

15 Claims, 1 Drawing Sheet

U.S. PATENT DOCUMENTS

| | | | |
|---|---|---|---|
| 4,772,691 A | 9/1988 | Herman | 540/145 |
| 4,886,831 A | 12/1989 | Morcos et al. | 514/456 |
| 4,897,444 A | 1/1990 | Brynes et al. | 525/54.1 |
| 4,905,670 A | 3/1990 | Adair | 128/18 |
| 4,920,143 A | 4/1990 | Levy et al. | 514/410 |
| 4,977,177 A | 12/1990 | Bommer et al. | 514/410 |
| 4,997,639 A | 3/1991 | Aizawa et al. | 424/9 |
| 5,026,368 A | 6/1991 | Adair | 606/15 |
| 5,043,101 A | 8/1991 | Gordon | 252/408.1 |
| 5,079,262 A | 1/1992 | Kennedy et al. | 514/561 |
| 5,087,636 A | 2/1992 | Jamieson et al. | 514/410 |
| 5,117,466 A | 5/1992 | Buican et al. | 382/6 |
| 5,122,453 A | 6/1992 | Martin et al. | 435/7.24 |
| 5,143,054 A | 9/1992 | Adair | 128/18 |
| 5,149,708 A | 9/1992 | Dolphin et al. | 514/410 |
| 5,211,938 A | 5/1993 | Kennedy et al. | 424/7.1 |
| 5,234,940 A | 8/1993 | Kennedy et al. | 514/410 |
| 5,251,613 A | 10/1993 | Adair | 128/6 |
| 5,270,171 A | 12/1993 | Cercek et al. | 435/29 |
| 5,283,255 A | 2/1994 | Levy et al. | 514/410 |
| 5,308,608 A | 5/1994 | Dolphin et al. | 424/9 |
| 5,308,861 A | 5/1994 | Aizawa et al. | 514/410 |
| 5,391,547 A | 2/1995 | Cole et al. | 514/184 |
| 5,399,583 A | 3/1995 | Levy et al. | 514/410 |
| 5,418,169 A | 5/1995 | Crissman et al. | 436/94 |
| 5,422,093 A | 6/1995 | Kennedy et al. | 424/9.61 |
| 5,441,531 A | 8/1995 | Zarate et al. | 607/90 |
| 5,554,505 A | 9/1996 | Hajek et al. | 435/721 |
| 5,556,764 A | 9/1996 | Sizto et al. | 435/7.24 |
| 5,591,422 A | 1/1997 | Hemmi et al. | 424/9.362 |
| 5,605,805 A | 2/1997 | Verwer et al. | 435/7.24 |
| 5,616,342 A | 4/1997 | Lyons | 424/450 |
| 5,627,040 A | 5/1997 | Bierre et al. | 435/7.24 |
| 5,652,114 A | 7/1997 | Chu et al. | 435/7.23 |
| 5,773,609 A | 6/1998 | Robinson et al. | 540/145 |
| 5,955,490 A | 9/1999 | Kennedy et al. | 514/410 |
| 5,993,774 A | 11/1999 | Archer et al. | 424/1.65 |
| 6,004,531 A | 12/1999 | Archer et al. | 424/1.65 |
| 6,190,877 B1 | 2/2001 | Adair | 435/29 |
| 6,235,767 B1 | 5/2001 | Kelly et al. | 514/410 |
| 6,350,431 B1 | 2/2002 | Snow et al. | 424/9.6 |
| 6,358,989 B1 | 3/2002 | Kunz et al. | 514/411 |
| 6,387,350 B1 | 5/2002 | Goldenberg | 424/1.57 |
| 6,395,016 B1 | 5/2002 | Oron et al. | 607/88 |
| 6,422,988 B1 | 7/2002 | Bradshaw et al. | 600/3 |
| 6,422,989 B1 | 7/2002 | Hektner | 600/3 |
| 6,566,517 B1 | 5/2003 | Miura et al. | 540/145 |
| 6,753,160 B1 * | 6/2004 | Adair | 435/29 |
| 2004/0202610 A1 | 10/2004 | Adair | |
| 2004/0202612 A1 | 10/2004 | Adair | |

OTHER PUBLICATIONS

Furmanski and Longley, *Cancer Res.*, 48:4604–4610 (1988).

Harisinghani et al., *N. Engl. J. Med.*, 348(25):2491–2499 (2003).

Koenig et al., *Magnetic Resonance in Medicine*, 4:252–260 (1987).

Lyon et al., *Magnetic Resonance in Medicine*, 4:24–33 (1987).

Rosenthal et al., *Clin. Cancer Res.*, 5:739–745 (1999).

van Zijl et al., *Acta Radiologica*, 374(supp):75–79 (1990).

Abstract, Mu Y, et al., "P–S–D–007 Luminescence in the Diagnosis of Exfoliative Cells from Malignant Tumors", X–P–0021614131, vol. 9, No. 4, 1987, pp. 258–259.

Abstract, Schwartz, G., et al., "Selected Amino Acridines as Fluorescent Probes in Cytochemistry in General and in the Detection of Cancer Cells in Particular", *Analytical and Quantitative Cytology*, vol. 4, No. 1, 1982, pp. 44–54.

Abstract, Gardiner, R.A., et al., "Abnormal prostatic cells in ejaculates from men with prostatic cancer: A preliminary report", *British Journal of Urology*, vol. 78, No. 3, 1996, pp. 414–418.

Abstract, Bologna, M., et al., "Improved tissue culture method for the study of prostatic carcinoma: A significant diagnostic tool.", *Pathology Research and Practice*, vol. 191, No. 9, 1995, pp. 899–903.

Abstract, Sauter, E.R., et al., "Nipple aspirate fluid: A promising non–invasive method to identify cellular markers of breast cancer risk", *British Journal of Cancer*, vol. 76, 1997, pp. 494–501.

Abstract, Sugiyama, M., et al., "Non–invasive detection of bladder cancer by identification of abnormal CD44 proteins in exfoliated cancer cells in urine", Abstract, *Clinical Molecular Pathology*, 1995, vol. 48, pp. M142–M147.

Nyamekye et al.; "Photodynamic Therapy of Normal and Balloon–Injured Rat Carotid Arteries Using 5–Amino–Levulinic Acid"; *Circulation*, vol. 91, No. 2, Jan. 15, 1995, pp. 417–425.

Peng et al.; "5–Aminolevulinic Acid–Based Photodynamic Therapy"; *American Cancer Society*; 1997; pp. 2282–2305.

Berg et al.; "The Influence of Iron Chelators On the Accumulation of Protoporphyrin IX in 5–Aminolaevulinic Acid–Treated Cells"; *British Journal of Cancer*; 1996; pp. 688–697.

Noodt et al.; "Apoptosis and Necrosis Induced With Light and 5–Aminolaevulinic Acid–Derived Protoporphyrin IX"; *Flow Cytometry*; 1996; pp. 22–29.

Malik et al.; "Destruction of Erythroleukaemic Cells by Photoactivation of Endogenous Porphyrins" *British Journal of Cancer*; 1987; 56; pp. 589–595.

Leon et al.; "Localized Intracoronary Gamma–Radiation Therapy to Inhibit the Rcurrence of Restenosis After Stenting"; *The New England Journal of Medicine*; Jan. 25, 2001; 344(4); pp. 250–256.

Verin et al.; "Endoluminal Beta–Radiation Therapy for the Prevention of Coronary Restenosis After Balloon Angioplasty"; *The New England Journal of Medicine*; Jan. 25, 2002; 344(4); pp. 243–249.

Abstract: Leunig et al.; "Fluorescence Photodetection of Neoplastic Lesions in the Oral Cavity Following Topical Application of 5–Aminolevulinic Acid"; *Laryngo–Rhino–Otologie*; vol. 75, No. 8, Aug. 1996; pp. 459–464.

Firnau et al.; "$^{64}$Cu Labelling of Hematoporphyrin Derivative for Non–Invasive In–Vivo Measurements of Tumour Uptake" *Porphyin Localizatikon and Treatment of Tumors*; 1984 Alan R. Liss, Inc.; pp. 629–636.

Kulkarni et al.; "Radio Indium and Gallium Labeled Porphyrins for Medical Imaging"; *AIP Conference Proceedings*; 2001; pp. 837–840.

Verin et al.; "Endoluminal Beta–Radiation Therapy for the Prevention of Coronary Restenosis After Balloon Angioplasty"; *The New England Journal of Medicine*; Jan. 25, 2001; 344(4); pp. 243–249.

* cited by examiner

METHOD OF USING METALOPORPHYRINS FOR TREATMENT OF ARTERIOSCLEROTIC LESIONS

CROSS REFERENCE TO RELATED APPLICATIONS

This application is a continuation-in-part of patent application Ser. No. 10/215,881, filed on Aug. 8, 2002 now U.S. Pat. No. 6,753,160, which is a continuation-in-part application of prior application Ser. No. 10/176,558, filed on Jun. 21, 2002 now U.S. Pat. No. 6,750,037, which are incorporated herein in their entirety by this reference.

FIELD OF THE INVENTION

This invention relates to use of radiopharmaceuticals in the treatment of arteriosclerotic lesions in blood vessels, and more particularly, to the use of metaloporphyrins wherein a porphyrin is complexed with a radioactive metal for targeted delivery of radiation to arteriosclerotic lesions.

BACKGROUND OF THE INVENTION

It is known that certain types of obstructions in arteries may be due, in part, to arteriosclerotic plaques. These plaques typically result from the proliferation of smooth muscle cells and associated fibrous tissue which invades the wall and lining cells (intima) of the artery. While the reasons for the smooth muscle and fibrous cell proliferation in the arterial walls is not completely understood, this proliferation is not generally considered to be neoplastic in origin, in spite of the fact that regeneration of plaque can take place very rapidly, sometimes within a few months of total removal by coronary endarterectomy.

Management of arteriosclerotic stenosis by balloon angioplasty is a common treatment method; however, the effectiveness of such treatment is limited by restenosis. Restenosis occurs in about 30% to 50% of patients having undergone angioplasty. Fibrocellular intimal hyperplasia is a main cause of such restenosis which arises from proliferation of smooth muscle cells in the intimal layer.

Porphyrins are a large class of typically red or purple fluorescent crystalline pigments, with natural or synthetic origin, having in common a substituted aromatic macrocyclic ring consisting of four pyrrole-type residues, linked together by four methine bridging groups. It is recognized that smooth muscle cells which proliferate in arteries have a distinct affinity for various porphyrin compounds such as HPD, photofrin, photofrin II, and a long list of other porphyrin compounds. A proliferating smooth muscle cell will take up such porphyrin compounds much in the same manner as cells which are either dysplastic or overtly malignant. Because these cells become sensitized by these porphyrin compounds, they are capable of responding to both photo-detection and photo-destruction when proper frequencies of light are administered. Use of this "photodynamic" therapy in the management of angioplasty restenosis in patients is described in *Photodynamic Therapy of Normal and Balloon Injured Rat Carotid Arteries Using 5-Amino-Levulinic Acid, Circulation*, 91(2):417–25 (1995), incorporated herein by this reference in its entirety for disclosing basic procedures for photodynamic therapy of arteriosclerotic abnormalities.

Although many physicians and researchers are familiar with photodynamic therapy and many have used such procedures in the laboratory, few have become advocates of the therapy because of the severe limitations imposed by the use of porphyrins which utilize light frequencies that do not penetrate, and are therefore impossible to deliver to any significant depth in tissue. The light frequencies required for photo detection generally range between 380–420 nm, and the resulting fluorescence is typically in the range of 635 nm. Because of these wavelengths, penetration of the light source is restricted to tissue of minimal depth in the body. Accordingly, without surgical intervention, phototherapy is not capable of effectively reaching arteriosclerotic lesions.

As also understood by those skilled in the art, photodynamic therapy has been used for treatment of various cancers. Examples of references which disclose use of photodynamic therapy for treatment of cancer include the U.S. Pat. Nos. 5,087,636 and 5,211,938.

Another significant, well known method for treatment of arteriosclerotic abnormalities includes localized intercoronary radiation therapy. This therapy is reviewed in *Localized Intercoronary Gamma Radiation Therapy to Inhibit the Recurrence of Restenosis after Stenting, and Endoluminal Beta Radiation Therapy for the Prevention of Coronary Restenosis after Balloon Angioplasty*, The New England Journal of Medicine, 344(4)243–56 (2001). The studies reported therein indicate significantly lowered rates of clinical and angiographic restenosis following radiation therapy.

There are also a number of references which further disclose radiation therapy for arteriosclerotic abnormalities including U.S. Pat. Nos. 6,422,989; 6,422,988; 6,935,016; 6,387,350; 6,358,989; and 6,235,767.

Finally, there is a known treatment for cancer which utilizes metaloporphyrins to deliver site selective radiation therapy. More specifically, U.S. Pat. No. 5,391,547 discloses a method for using porphyrins to detect lung cancer by the use of tetra-aryl porphyrins. The porphyrins are used as fluorescent tracers for cancers of the lung. The porphyrins are complexed with $^{64}$Cu or $^{67}$Cu. Thus, the complex can be used as radiotracers as well. The $^{67}$Cu provides a source of beta radiation for selective destruction of lung malignancies as well as gamma radiation useful for image analysis, as by a single photon emission computed tomography (SPECT). The $^{64}$Cu as a positron emitter, may be used for radiotracing wherein positron emission tomography (PET) techniques can be used to locate the malignant tissue.

While the aforementioned radiation treatments for arteriosclerotic abnormalities have shown some promise, one significant drawback to known procedures is the inability to effectively localize the radio compounds in the targeted tissue. Furthermore, such radiation treatment is typically done after there has already been an interventional procedure conducted, such as balloon angioplasty or stent emplacement. Thus, such radiation is primarily used as a follow-up treatment and not an initial treatment of arteriosclerotic abnormalities.

While photodynamic therapy also has been proven to be effective in prevention of arteriosclerosis, photodynamic therapy in practice is extremely difficult to incorporate because an illuminating catheter must be delivered to the damaged arterial locations and even after the catheter has reached the site to be treated, normal blood flow through the arteries further complicates the ability to deliver an effective intensity of light to the targeted tissue.

Therefore, while photodynamic therapy and radiation treatment can potentially be effective, there is still a need for a non-interventional procedure for treatment of arteriosclerotic abnormalities which provides not only an initial screening or diagnosis, but also may be simultaneously used for actual treatment of the affected blood vessels to reduce and destroy plaque and prevent or eliminate restenosis.

SUMMARY OF THE INVENTION

The present invention provides a method for diagnosis, visualization and treatment for arteriosclerotic abnormalities. The method is non-invasive and can be utilized to remove arteriosclerotic plaque at any inter-arterial site in the body. This new modality of treatment can be directed at arteries which have had no previous surgical intervention, as well as those sites which have been previously treated such as by balloon angioplasty or stent emplacement.

The present invention makes use of porphyrin compounds complexed with various metals such as silver (Ag), aluminum (Al), cadmium (Cd), cobalt (Co), chromium (Cr), copper (Cu), iron (Fe), gadolinium (Gd), indium (In), lutetium (Lu), magnesium (Mg), manganese (Mn), nickel (Ni), palladium (Pd), platinum (Pt), rhodium (Rh), ruthenium (Ru), scandium (Sc), silicon (Si), tin (Sn), titanium oxide (TiO), vanadium oxide (VO), ytterbium (Yb) and zinc (Zn). These complexes are generally categorized as metaloporphyrins meaning a porphyrin moiety having a chelated metal atom. The metaloporphyrins of the present invention are further processed so that the metal is in the form of a radioactive isotope. The resulting radioactive metaloporphyrins thereby constitute radiopharmaceuticals that can be intravenously administered to the patient. The affinity of the smooth muscle cells and fibrous tissue (plaque) for porphyrins results in selective uptake of the radioactive metaloporphyrin, thereby effecting targeted delivery of therapeutic radiopharmaceuticals to plaque lesions. In the instance of elemental copper chelated by the porphyrin, the copper can be transformed to radioactive $^{67}Cu$ or $^{64}Cu$. In this way, introduction of the metaloporphyrin radiopharmacuetical to the patient is an effective means of targeted or site-selective delivery of measured radiation therapy to the targeted arteriosclerotic tissue. Additionally, these metaloporphyrin complexes still provide the ability to simultaneously conduct fluorescence detection and phototherapy if desired. Also, the metaloporphyrins provide the ability for observation of the areas of plaque buildup through PET scanning or SPECT scanning. Metaloporphyrins complexed with radioactive metals, also provide a source of radiation for the selective destruction of plaque sites.

Accordingly, the method of the invention provides a non-invasive (non-surgical) procedure, and also provides various options for initial diagnosis and treatment of plaque buildup. The natural affinity of the proliferating tissues for the porphyrin compounds provides an effective means for delivering radiation to the affected tissue.

DETAILED DESCRIPTION OF THE INVENTION

Figure 1:
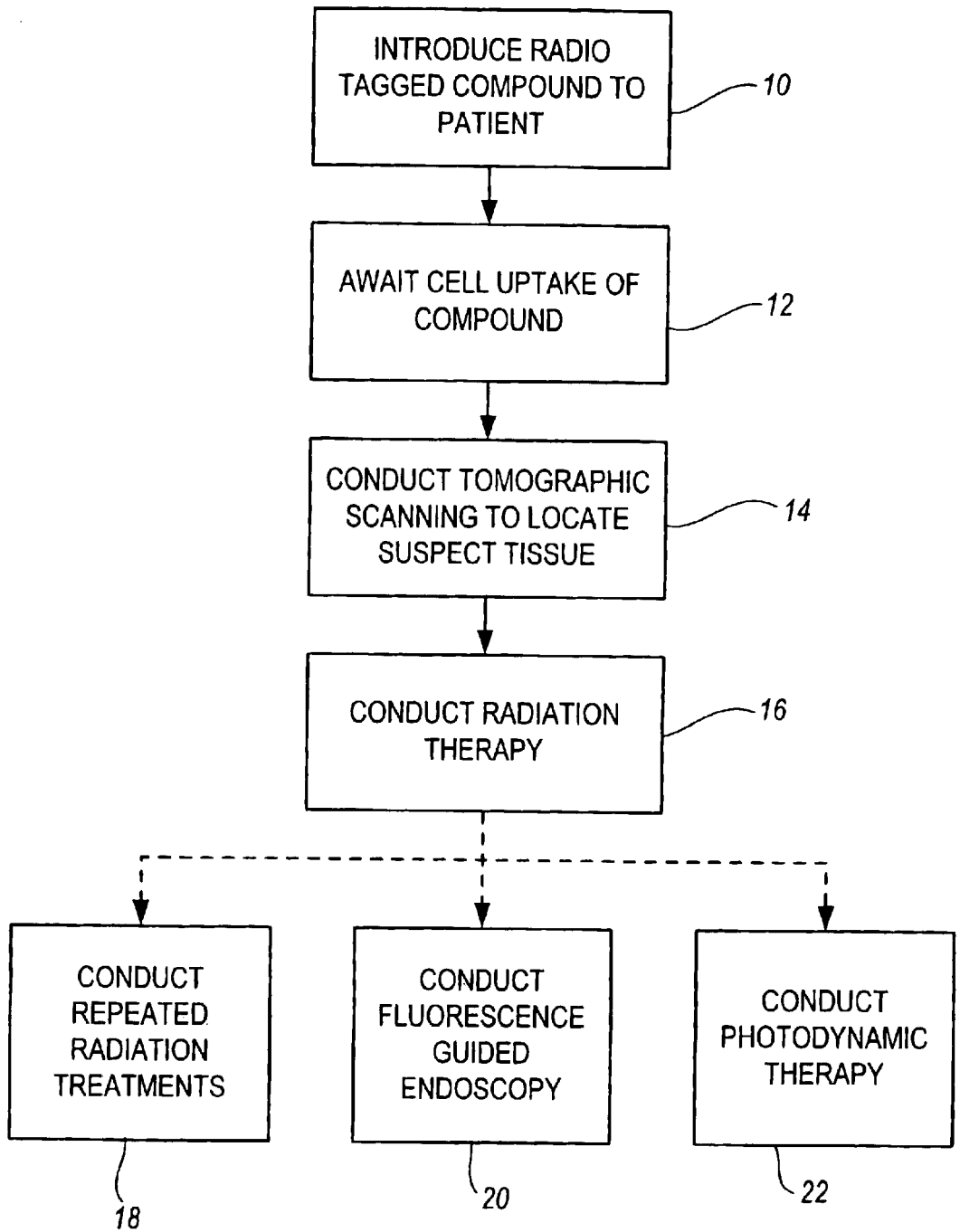
FIG. 1 is a simplified flow diagram illustrating the major steps in the method by use of the porphyrin complexes for radio tracing through scanning and radiation therapy.

In addition to use of known porphyrins, a number of additional photo-sensitive compounds may be complexed with selected metals. These additional compounds include, without limitation, 5-amino levulenic acid (5-ALA), protoporphyrin IX, TCPP, hematoporphyrin derivative, photofrin, photofrin II, uroporphyrin, coproporphyren, tetraphenylporphinesulfonate (TPPS) and tetraporphen (4, N-methylulpyridil) (TMPP). Each of these photosensitive compounds, to include the below listing of metaloporphyrins are available from Frontier Scientific (formerly Porphyrin Products), of Logan Utah. These commercially available metaloporphyrins are further treated to convert the elemental metals to radioactive isotopes. Conversely, these radioactive metaloporphyrins useful as radiopharmaceutical agents may be formed by purchasing or isolating radioactive metals of interest which are then combined with the desired porphyrin molecules to form radioactive metaloporphyrins. U.S. Pat. No. 5,391,547 is hereby incorporated by reference for purposes of disclosing the use of metaloporphyrins and the methods by which metaloporphyrins are manufactured and combined with metal isotopes. Some of the metaloporphyrins suitable for use in the present invention that are commercially available through Frontier Scientific include Protoporphyrin IX and derivatives thereof including Protoporphyrin IX Dimethyl Ester, Protoporphyrin IX Acid, and Protoporphyrin IX Na Salt; Porphine; Octaethylporphine; Hematoporphyrin IX and derivatives thereof including Hematoporphyrin D and Hematoporphyrin IX Dimethyl Ester; Etioporphyrin and Etioporphyrin I; meso-Tetraphenylporphine and derivatives thereof including meso-Tetra (N-methyl-4-Pyridyl)porphine, meso-Tetra (4-Pyridyl)porphine, meso-Tetra (4-sulfonatophenyl) porphine and meso-Tetra (4-carboxyphenyl)porphine; Coproporphyrin I and Coproporphyrin III; Deuteroporphyrin IX and derivatives thereof including Deuteroporphyrin IX Bis Glycol and Deuteroporphyrin Disulfonic Acid; Mesoporphyrin IX; Tetra Tosylate; Uroporphyrin I; and Iso-hematoporphyrin IX. Each of these porphyrins may be complexed with a radioactive isotope as desired.

Referring to FIG. 1, the first step in the method is to introduce the radio tagged porphyrin compound to a patient having been diagnosed with, or having a suspected plaque buildup. The administration may be conducted by intravenous administration of the porphyrin radiopharmaceutical or may be conducted through a catheter specifically placed to direct the porphyrin radiopharmaceutical to a specific arterial site within the patient. This is shown as step 10. The necessary period of time is then given to allow cell uptake of the compound, shown at block 12. In block 14, tomographic scanning can be conducted to determine sites of plaque buildup. If no appreciable arteriosclerotic abnormalities are observed, then the procedure is complete; however, if arteriosclerotic abnormalities are found, delivery of the radio tagged compound results in selective ionizing radiation of the intra-arterial tissue occurring, shown at step 16. As necessary, step 16 can be repeated by repeated introduction of the radio-tagged porphyrin compound or the further introduction of a different radio-tagged porphyrin compound, thereby enabling a selective number of radiation treatments to take place in order to destroy the targeted tissue. Repeated radiation treatment is shown as optional step 18. Although step 16 is shown as a separate step, it shall be understood that the radiation treatment takes place simultaneously each time a patient is provided the radio-tagged porphyrin compound, even with the initial administration. Additionally, for each necessary radiation therapy treatment, the particular metaloporphyrin can be dosed with the desired amount and type of radioactive material thereby providing adjustability for delivering the desired amount of radiation and type of radiation. As also mentioned above, if it were desired to actually visualize the destruction of the targeted tissue, an interventional procedure could take place such as by introduction of a catheter to the targeted area. Using photo-detection methodology, the tissue can be observed to confirm the results of the treatment. This optional step is shown as step 20. Additionally, photo-dynamic therapy could also be conducted if an interventional procedure was performed to record and/or confirm the results of the procedure. This is shown as optional step 22. Further, an interventional procedure such as balloon angioplasty or stent emplacement can be augmented by the use of the porphyrin radiopharmaceuticals of the present invention. By this means, the porphyrin radiopharmaceuticals are administered prior to or after performing the interventional procedure to enhance the benefits gained from the interventional therapy and to decrease or eliminate the rate of restenosis seen following these procedures.

The ability to simultaneously conduct a non-interventional diagnostic procedure and to simultaneously provide treatment is a very clear advantageous use of metaloporphyrins in diagnosing and treating arteriosclerotic abnormalities. The porphyrin which is used as a carrier for delivering the radiation to the patient also helps to localize the radioactive material in the tissue that requires the treatment. As described in U.S. Pat. No. 5,391,547, these porphyrin-based therapeutic agents may additionally localize to cancers of the lung. Thus, as an additional benefit of the therapeutic treatment of arteriosclerotic plaque, these metaloporphyrin radiopharmaceuticals may additionally detect and treat any cancerous tissue present in patients in need of treatment for arteriosclerotic plaque.

Beta emitters, such as iodine-131 ($^{131}$I), yttrium-90 ($^{90}$Y), copper-67 ($^{67}$Cu) and rhenium-186 ($^{186}$Re) have radiation safety advantages in that the beta particles do not penetrate tissue far enough that significant damage is done to healthy tissues. Alpha emitters, such as astatine-211 ($^{211}$At) and bismuth-212 ($^{212}$Bi), deliver larger doses to normal and arteriosclerotic tissue. Gamma emitters provide the energy necessary to image the arteriosclerotic tissues which the metaloporphirins have accumulated in but may not be cytotoxic enough to kill that tissue thereby preventing the use of many gamma emitters for therapy. For example, gallium-67 and indium-111 are gamma emitters routinely used for medical imaging but are generally too weak to produce therapeutic effects. Alternatively, copper-67 releases abundant beta particles suitable for radiotherapy as well as gamma emissions suitable for diagnostic imaging. Low energy x-ray emitters such as $^{125}$I reduce the risks of damage to healthy tissues but high doses must be used to achieve a therapeutic outcome.

The therapeutic compounds of the present invention can be administered to a patient alone or in combination with pharmaceutically acceptable carriers, the proportion of which is determined by the solubility and chemical nature of the compound and standard pharmaceutical practice. The physician will determine the ultimate dosage of these therapeutic agents which will be most suitable for prophylaxis or treatment and will vary with the form of administration and the particular compound chosen, and also, with the particular patient under treatment. The physician will generally aim to initiate treatment with the lowest dose that will successfully treat the arteriosclerotic lesion. For the radioactive compounds of the present invention, the dose is measured by the radioactivity emitted by the compound. Thus, the weight of the metaloporphyrin and the coordinated metal is not used in determining the proper treatment dosage. For most patients, the effective range of therapeutic dosages is between about 5 Gy and 25 Gy of radiation. Typically, the range is between about 9 Gy and about 18 Gy. Preferably, the range is between about 15 Gy and about 20 Gy.

Referring specifically to the use of isotopes of copper, a metaloporphyrin complexed with $^{67}$Cu provides not only the ability to conduct visualization through SPECT scanning, but the $^{67}$Cu also provides beta radiation for purposes of providing radiation therapy. Alternatively, $^{64}$Cu decays by electron capture, and beta decay accompanied by emission of radiation and gamma photons and can be used for treatment and for purposes of conducting PET scanning. Therefore, it is also contemplated within the spirit and scope of the invention to provide metaloporphyrins for tomographic scanning and for radiation treatment. Thus, it is also contemplated that the radioactive metals within the metaloporphyrin complexes may be selected for the production of gamma, positron, and beta emissions as desired to enable the desired type of tomographic scanning, as well as radiation therapy. Moreover, it is possible to use a first radioactive metaloporphyrin for diagnosis and treatment of arteriosclerotic plaque followed by the use of a second radioactive metalophophyrin for the visualization of arteriosclerotic plaque to monitor treatment progression. In this way, the porphyrin and/or the radioactive isotope may be chosen due to their respective suitability for the procedure performed; either detection or destruction of the arteriosclerotic tissue. For example, the initial diagnosis and treatment may be conducted with a $^{64}$Cu-containing porphyrin or a $^{67}$Cu-containing porphyrin while any subsequent visualization of arteriosclerotic plaque may be performed with $^{111}$In-containing porphyrin. Further to modifying or selecting the porphyrin and intercalated radioactive isotope for specific procedures, the porphyrin and isotope may be selected for repetition of the therapy. Finally, it is contemplated that the therapy may also be modified in number and frequency of repetitive treatments based on the porphyrin and/or radioactive isotope used.

This application has been described with respect to a preferred embodiment; however, various modifications can be made which fall within the spirit and scope of the invention.

What is claimed is:

1. A method of treating arteriosclerotic disease comprising administering a therapeutically effective dose of a cytotoxic compound comprising a porphyrin complexed with a radioactive metal to a mammal.

2. The method of claim 1, wherein the radioactive metal is selected from the group consisting of $^{67}$Cu, $^{64}$Cu, $^{131}$I, $^{131}$Y, $^{186}$Re, $^{211}$At, $^{212}$Bi and $^{125}$I.

3. The method of claim 1, wherein the radioactive metal is $^{64}$Cu.

4. The method of claim 1, wherein the radioactive metal is $^{67}$Cu.

5. The method of claim 1, wherein the prophyrin is selected from the group consisting of protoporphyrin IX, TCPP, hematoporphyrin derivative, photofrin, uroporphyrin, coproporphyrin, TPPS, and TMPP.

6. The method of claim 1, wherein the therapeutically effective dose is between about 5 Gy and about 25 Gy of radiation.

7. The method of claim 1, wherein the therapeutically effective dose is between about 9 Gy and about 18 Gy of radiation.

8. The method of claim 1, further comprising the step of: conducting tomographic imaging of the mammal after the administering step.

9. The method of claim 8, further comprising the step of:
administering a compound comprising a porphyrin complexed with a radioactive metal to the mammal after the conducting tomographic imaging step;
conducting tomographic imaging of the mammal; and,
comparing imaging results from tomographic imaging conducted following administration of the cytotoxic compound with imaging results from tomographic imaging conducted following administration of the compound to assess treatment results.

10. A method, as claimed in claim 8, wherein the tomographic imaging is positron emission tomography.

11. A method, as claimed in claim 8, wherein the tomographic imaging is single photon emission computed tomography.

12. A radiopharmaceutical composition for the treatment of arteriosclerosis comprising a porphyrin complexed with a cytotoxic radiation-emitting metal selected from the group consisting of $^{67}$Cu, $^{64}$Cu, $^{131}$I, $^{90}$Y, $^{186}$Re, $^{211}$At, $^{212}$Bi and $^{125}$I.

13. The radiopharmaceutical composition of claim 12, wherein the porphyrin is selected from the group consisting of Protoporphyrin IX; Porphine; Octaethylporphine; Hematoporphyrin IX; Etioporphyrin; Etioporphyrin I; meso-Tetraphenylporphine; Coproporphyrin I; Coproporphyrin III; Deuteroporphyrin IX; Mesoporphyrin IX; Tetra Tosylate; Uroporphyrin I; and Iso-hematoporphyrin IX.

14. A method of treating arteriosclerotic disease comprising administering a therapeutically effective dose of a cytotoxic compound comprising a porphyrin complexed with a radioactive metal to a mammal, wherein said radioactive metal does not have gamma emissions as its primary mode of decay.

15. A method of treating arteriosclerotic disease comprising administering a therapeutically effective dose of a cytotoxic compound comprising a porphyrin complexed with a radioactive metal to a mammal, wherein said radioactive metal is selected from the group consisting of an alpha emitter, a beta emitter, and a combined beta and gamma emitter.

* * * * *